United States Patent
Klun et al.

(10) Patent No.: US 6,562,841 B1
(45) Date of Patent: May 13, 2003

(54) METHODS AND COMPOSITIONS FOR REPELLING ARTHROPODS

(75) Inventors: Jerome A. Klun, Potomac, MD (US); Walter F. Schmidt, Beltsville, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/978,154

(22) Filed: Oct. 16, 2001

Related U.S. Application Data (60) Provisional application No. 60/241,642, filed on Oct. 19, 2000.

(51) Int. Cl.$^7$ .................. A01N 43/40; A61K 31/445
(52) U.S. Cl. ........................... 514/315; 514/330
(58) Field of Search .................. 424/405; 514/315, 514/330

(56) References Cited

U.S. PATENT DOCUMENTS

| | | | |
|---|---|---|---|
| 4,797,408 A | 1/1989 | McGovern et al. | 514/315 |
| 5,008,261 A | 4/1991 | Kruger et al. | 514/212 |

OTHER PUBLICATIONS

Frances et al, Field evaluation of repellent, 1999, J. Am. Mosq. Control Assoc., 15(3), 339–341.*
Schreck et al, Repellents and other personal protection, 1989, J. Am. Mosq. Control Assoc., 5(2), 247–250.*
Allinger, N.L., et al., "Molecular Mechanics. The MM3 Force Field for Hydrocarbons", *J. American Chemical Society*, vol. 111(23), pp. 8551–8566, Nov. 8, 1989.
Coleman, R.E., et al., "Laboratory Evaluation of Repellents Against Four Anopheline Mosquitoes (Diptera: Culicidae) and Two Phlebotomine Sand Flies (Diptera: Psychodidae)", *J. Medical Entomology*, vol. 30(3), pp. 499–502, May 1993.
Frances, S.P., et al., "Laboratory and Field Evaluation of the Repellents Deet, CIC–4, and AI3–37220 Against *Anopheles farauti*(Diptera: Culicidae) in Australia", *J. Medical Entomology*, vol. 35(5), pp. 690–693, Sep. 1998.
Frances, S.P., et al., "Laboratory and Field Evaluation of Deet, CIC–4, and AI3–37220 Against Anopheles dirus (Diptera:Culicidae) in Thailand", *J. Medical Entomology*, vol. 33, pp. 511–515, Jul. 1996.
Harris, R.K., "Nuclear Magnetic Resonance Spectroscopy, A Physiochemical View", Longman Scientific & Techincal, Longman Group UK Limited, pp. 121–127, 1986.
Hoch, A.L., et al., "Laboratory Evaluation of a New Repellent Camouflage Face Paint", *J. American Mosquito Control Association*, vol. 11(2), pp. 172–175, Jun. 1995.

Klun, J.A., et al., "A New Module for Quantitative Evaluation of Repellent Efficacy Using Human Subjects", *J. Medical Entomology*, vol. 37(1), pp. 177–181, Jan. 2000.
Klun, J.A., et al., "Optically Active Arthropod Repellents for Use Against Disease Vectors", *J. Medical Entomology*, vol. 37(1), pp. 182–186, Jan. 2000.
McGovern, T.P., et al., "Mosquito Repellents: Alicyclic Amides as Repellents For *Aedes aegypti* and *Anopheles quadrimaculatus*", *Mosquito News*, pp. 346–349, Sep. 1978.
Robert, L.L., et al., Toxicology Study No. 86–8104–98, "Laboratory and Field Evaluation of Five Repellents Against the Black Flies *Prosimulium mixtum* and *P. fuscum* (Diptera: Simuliidae)", *J. Medical Entomology*, vol. 29(2), pp. 267–272, Mar. 1992.
Snodgrass, H.L., et al., "The Acute Toxicity of the Diastereomers of the Insect Repellent AI3–37220", *U.S. Army Center for Health Promotion and Preventive Medicine*, pp. 1–7, Jun. 1998.
Vries, T., et al., "The Family Approach to the Resolution of Racemates", *Angew. Chem. Int. Ed.*, vol. 37(17), pp. 2349–2354, 1998.
Walker, T.W., et al., "Field Evaluation of Arthropod Repellents, Deet and A Piperidine Compound, AI3–37220, Against *Anopheles funestus* and *Anopheles arabiensis* in Western Kenya", *J. American Mosquito Control Association*, vol. 12(2), pp. 172–176, Jul. 1996.
Schreck, C.E., et al., "Repellents and Other Personal Protection Strategies Against *Aedes albopictus*", J. American Mosquito Control Association, vol. 5(2), pp. 247–250, Jun. 1989.
Frances, S.P., et al., "Field Evaluation of the Repellents Deet, CIC–4, and AI3–37220 Against Anopheles in Lae, Papua New Guinea", *J. American Mosquito Control Association*, vol. 15(3), pp. 339–341, Sep. 1999.

\* cited by examiner

*Primary Examiner*—Alton Pryor
(74) *Attorney, Agent, or Firm*—M. Howard Silverstein; John D. Fado; G. Byron Stover (57) ABSTRACT

A method for selecting the most effective arthropod repellent from stereoisomers of a compound, involving testing each stereoisomer of the compound for its effectiveness as an arthropod repellent against an arthropod of a particular genus and species, comparing the test results and selecting the most effective arthropod repellent stereoisomer from the stereoisomers of the compound, wherein the compound is a piperidine analog. A composition for repelling arthropods, containing a carrier material and an arthropod repelling effective amount of a stereoisomer of a compound, wherein said stereoisomer is selected by the above method. A method for repelling arthropods (e.g., *Aedes aegypti* or *Aedes albopictus*) from a mammal, involving treating the mammal with an arthropod with the above repelling composition (e.g., containing (1S,2'S) stereoisomer of 1-(3-cyclohexen-1-ylcarbonyl)-2-methylpiperidine).

21 Claims, 3 Drawing Sheets

(A): (1S,2'S-220) Conformer I      (B): (1S,2'S)-220 Conformer II

Fig. 3

METHODS AND COMPOSITIONS FOR REPELLING ARTHROPODS

REFERENCE TO RELATED APPLICATION

This application claims the benefit of U.S. Provisional Application No. 60/241,642, filed Oct. 19, 2000, which is incorporated herein by reference in its entirety.

BACKGROUND OF THE INVENTION

The present invention relates to a method for selecting the most effective arthropod repellent from stereoisomers of a compound, involving testing each stereoisomer of the compound for its effectiveness as an arthropod repellent against an arthropod of a particular genus and species, comparing the test results and selecting the most effective arthropod repellent stereoisomer from the stereoisomers of the compound, wherein the compound is a piperidine analog of the formula (I)

in which $R_2$, $R_3$, $R_4$, $R_5$ and $R_6$ may be the same or different and represent hydrogen, methyl, ethyl, isopropyl, or butyl groups, wherein said methyl, ethyl, isopropyl, or butyl groups are optionally substituted in their primary or secondary position with a hydroxyl (—OH) group, and $R_1$ represents unbranched or branched C1–8 alkanes, unbranched or branched C1–8 alkenes, C5–8 cycloalkanes, C5–8 cycloalkenes, methyl substituted C5–8 cycloalkanes, or methyl substituted C5–8 cycloalkenes or $R_1$ is —O—$R_7$ wherein a carbon atom of $R_7$ is attached to the O of —O—$R_7$ and wherein $R_7$ represents unbranched C1–8 alkanes, branched C1–8 alkanes, unbranched C1–8 alkenes, branched C1–8 alkenes, C5–8 cycloalkanes, C5–8 cycloalkenes, methyl substituted C5–8 cycloalkanes, or methyl substituted C5–8 cycloalkenes, and wherein said compound has at least one asymmetric center. Generally, the compound has one or two asymmetric centers.

The present invention also relates to a composition for repelling arthropods, containing a carrier material and an arthropod repelling effective amount of a stereoisomer of a compound selected by the above method.

In addition, the present invention also relates to a method for repelling arthropods from an object (e.g., mammals such as humans) or area (e.g., a surface such as human skin), involving treating the object or area with the above composition.

Figure 1:
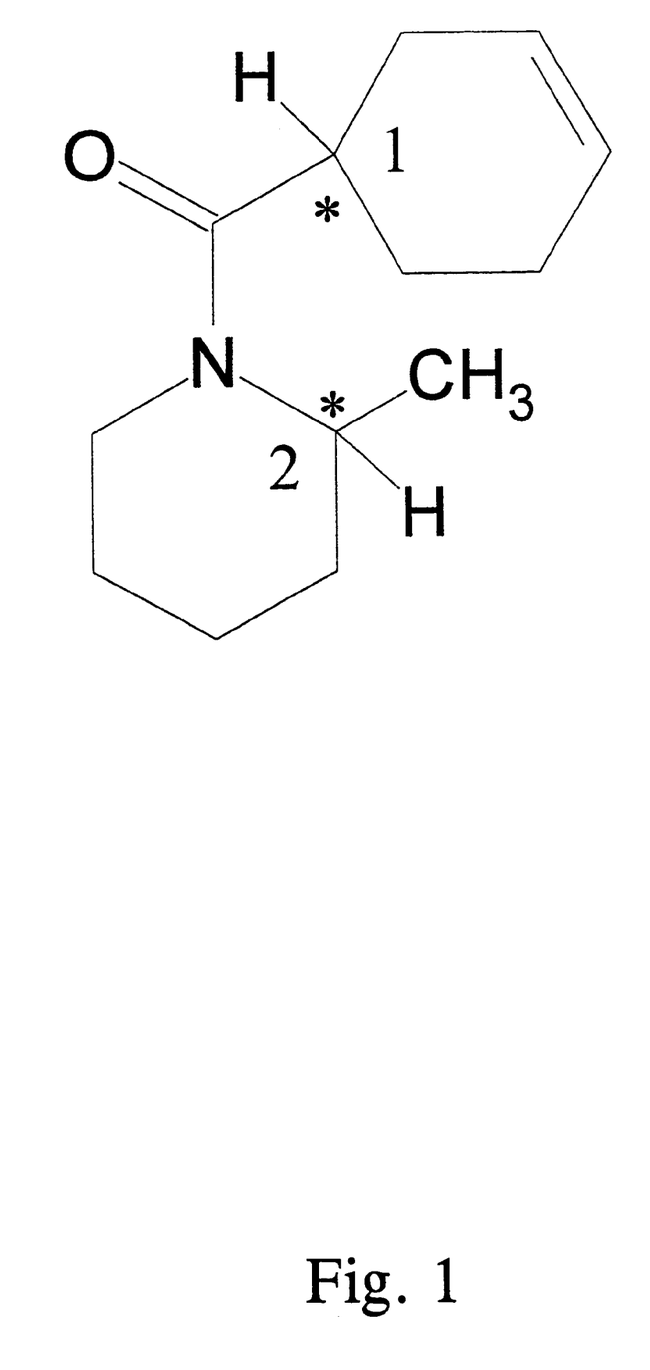
FIG. 1 shows the chemical structure of racemic 220, asymmetric carbon atoms are adjacent to the numbers in the two rings that comprise 220.

Racemic 1-(3-cyclohexen-1-ylcarbonyl)-2-methylpiperidine was first identified as an insect repellent twenty-two years ago (McGovern, T. P., et al., Mosq. News, 38: 346–349 (1978)). The U.S. Department of Agriculture assigned the compound a code number, AI3-37220, hereafter referred to as 220 (FIG. 1). The so-called repellent does not necessarily reduce the number of blood-sucking arthropods visiting a site where the compound has been applied, but it does reduce the number of bites sustained by an individual whose skin has been treated topically with the compound; the term repellent is used herein in this context. Field and laboratory studies against many species of blood-sucking arthropods have consistently shown that 220 is more or as effective as the commonly used arthropod repellent deet (N,N-diethyl-3-methyltoluamide) in reducing bites (Robert, L. L., et al., J. Med. Entomol., 29: 267–272 (1992); Coleman, R. E., et al., J. Med. Entomol., 30(3): 499–502 (1993); Walker, T. W., et al., J. Am. Mosq. Control. Assoc., 12: 172–176 (1996); Frances, S. P., et al., J. Med. Entomol. 33, 511–515 (1996); Frances, S. P., et al., J. Am. Entomol., 35(5): 690–693 (1998)).

Compound 220 contains two asymmetric centers and standard symmetric synthesis yields a equal mixture of four stereoisomers. All previous repellent studies were conducted using the stereoisomeric mixture (racemate). Up to now, the repellent properties of the individual stereoisomers of 220 or of other known repellents were never evaluated. The present study determined if chirality plays a role in repellents (e.g., 220).

SUMMARY OF THE INVENTION

A method is disclosed for selecting the most effective arthropod repellent from stereoisomers of a compound, involving testing each stereoisomer of the compound for its effectiveness as an arthropod repellent against an arthropod of a particular genus and species, comparing the test results and selecting the most effective arthropod repellent stereoisomer from the stereoisomers of the compound, wherein the compound is a piperidine analog of the formula (I)

in which $R_2$, $R_3$, $R_4$, $R_5$ and $R_6$ may be the same or different and represent hydrogen, methyl, ethyl, isopropyl, or butyl groups, wherein said methyl, ethyl, isopropyl, or butyl groups are optionally substituted in their primary or secondary position with a hydroxyl (—OH) group, and $R_1$ represents unbranched or branched C1–8 alkanes, unbranched or branched C1–8 alkenes, C5–8 cycloalkanes, C5–8 cycloalkenes, methyl substituted C5–8 cycloalkanes, or methyl substituted C5–8 cycloalkenes or $R_1$ is —O—$R_7$ wherein a carbon atom of $R_7$ is attached to the O of —O—$R_7$ and wherein $R_7$ represents unbranched C1–8 alkanes, branched C1–8 alkanes, unbranched C1–8 alkenes, branched C1–8 alkenes, C5–8 cycloalkanes, C5–8 cycloalkenes, methyl substituted C5–8 cycloalkanes, or methyl substituted C5–8 cycloalkenes, and wherein said compound has at least one asymmetric center. Generally, the compound has one or two asymmetric centers.

A composition is disclosed for repelling arthropods, containing a carrier material and an arthropod repelling effective amount of a stereoisomer of a compound selected by the above method.

A method is also disclosed for repelling arthropods from mammals, involving treating the mammal with the above composition.

DETAILED DESCRIPTION OF THE INVENTION

A method is disclosed for selecting the most effective arthropod repellent from stereoisomers of a compound, involving testing each stereoisomer of the compound for its effectiveness as an arthropod repellent against an arthropod of a particular genus and species, comparing the test results and selecting the most effective arthropod repellent stereoisomer from the stereoisomers of the compound, wherein the compound is a piperidine analog of the formula (I)

in which $R_2$, $R_3$, $R_4$, $R_5$ and $R_6$ may be the same or different and represent hydrogen, methyl, ethyl, isopropyl, or butyl groups, wherein said methyl, ethyl, isopropyl, or butyl groups are optionally substituted in their primary or secondary position with a hydroxyl (—OH) group, and $R_1$ represents unbranched or branched C1–8 alkanes, unbranched or branched C1–8 alkenes, C5–8 cycloalkanes, C5–8 cycloalkenes, methyl substituted C5–8 cycloalkanes, or methyl substituted C5–8 cycloalkenes or $R_1$ is —O—$R_7$ wherein a carbon atom of $R_7$ is attached to the O of —O—$R_7$ and wherein $R_7$ represents unbranched C1–8 alkanes, branched C1–8 alkanes, unbranched C1–8 alkenes, branched C1–8 alkenes, C5–8 cycloalkanes, C5–8 cycloalkenes, methyl substituted C5–8 cycloalkanes, or methyl substituted C5–8 cycloalkenes, and wherein said compound has at least one asymmetric center. Generally, the compound has one or two asymmetric centers.

Preferably, $R_2$, $R_3$, $R_4$, $R_5$, and $R_6$ may be the same or different and are hydrogen, methyl or —CH$_2$—CH$_2$—OH, and $R_1$ is 3-cyclohexene, —CH=C(CH$_3$)$_2$ or —O—$R_7$ where $R_7$ is a unbranched or branched $C_4$ alkane (preferably the O— is attached to carbon atom number 2 of the $C_4$ alkane). More preferably, (1) $R_3$, $R_4$, $R_5$, and $R_6$ are hydrogen, $R_2$ is —CH$_3$, and $R_7$ is 3-cyclohexene, there are four possible stereoisomeric forms of this compound; (2) $R_2$, $R_3$, $R_4$, $R_5$, and $R_6$ are hydrogen and $R_1$ is 3-cyclohexene, there are two possible stereoisomeric forms of this compound; (3) $R_3$, $R_4$, $R_5$, and $R_6$ are hydrogen, $R_2$ is —CH$_2$—CH$_2$—OH, and $R_7$ is a $C_4$ unbranched alkane with O— attached to carbon atom number 2 of the $C_4$ alkane, there are four possible stereoisomeric forms of this compound; or (4) $R_3$, $R_4$, and $R_5$ are hydrogen, $R_2$ and $R_6$ are —CH$_3$, and $R_1$ is —CH=C(CH$_3$)$_2$, there are four possible stereoisomeric forms of this compound. More preferably, the compound is 1-(3-cyclohexen-1-ylcarbonyl)piperidine or 1-(2-butoxycarbonyl)-2-(2-hydroxyethyl)-piperidine or 1-(3-cyclohexen-1-ylcarbonyl)-2-methylpiperidine. Most preferably the compound is 1-(3-cyclohexen-1-ylcarbonyl)-2-methylpiperidine.

Generally, prior to testing each stereoisomer of the compound for its effectiveness as an arthropod repellent against an arthropod of a particular genus and species (e.g., Aedes species such as Aedes aegypti (Linnaeus)), each stereoisomer is isolated from a racemic mixture containing the stereoisomers of the compound or each stereoisomer is individually prepared.

A composition is disclosed for repelling arthropods, containing a carrier material and an arthropod repelling effective amount of a stereoisomer of a compound (e.g., (1S,2'S) stereoisomer of 1-(3-cyclohexen-1-ylcarbonyl)-2-methylpiperidine) selected by the above method. The term "repelling" is defined as reducing the number of arthropod (e.g., Aedes aegypti (Linnaeus)) bites on a treated area or object (e.g., mammalian skin which has been treated topically with the compound of the present invention) when compared to the same area or object which is untreated.

A method is disclosed for repelling arthropods from an object (e.g., mammals such as humans) or area (e.g., a surface such as human skin), involving treating the object or area with the above composition.

The compositions can therefore be used for repelling harmful or troublesome arthropods such as blood-sucking and biting insects, ticks and mites.

The blood-sucking insects include mosquitoes (for example Aedes, Culex and Anopheles species), owl gnats (Phlebotoma), blackfly (Culicoides species), buffalo gnats (Simulium species), biting flies (for example Stomoxys calcitrans), tsetse flies (Glossina species), horseflies (Tabanus, Haematopota and Chrysops species), house flies (for example Musca domestica and Fannia canicularis), meat flies (for example Sarcophaga carnaria), flies which cause myiasis (for example Lucilia cuprina, Chrysomyia chloropyga, Hypoderma bovis, Hypoderma lineatum, Dermatobia hominis, Oestrus ovis, Gasterophilus intestinalis and Cochliomyia hominovorax), bugs (for example Cimex lectularius, Rhodnius prolixus and Triatoma infestans), lice (for example Pediculus humanus, Haematopinus suis and Damalina ovis), louse flies (for example Melaphagus orinus), fleas (for example Pulex irritans, Cthenocephalides canis and Xenopsylla cheopis) and sand fleas (for example Dermatophilus penetrans).

The biting insects include cockroaches (for example Blattella germanica, Periplaneta americana, Blatta orientalis and Supella supellectilium), beetles (for example Sitophilus granarius, Tenebrio molitor, Dermestes lardarius, Stegobium paniceum, Anobium puntactum and Hylotrupes bajulus), termites (for example Reticulitermes lucifugus) and ants (for example Lasius niger).

The ticks include, for example, Ornithodorus moubata, Ixodes ricinus, Boophilus microplus and Amblyomma hebreum, and mites include, for example, Sarcoptes scabiei and Dermanyssus gallinae.

The active compounds (e.g., most effective stereoisomer repellents) according to the invention, which can be used in undiluted or diluted form, can be converted into formulations customary for repellents. They can be used in all the presentation forms customary in cosmetics, for example in the form of solutions, emulsions, gels, ointments, pastes, creams, powders, sticks, sprays or aerosols from spray cans.

For use in the non-cosmetic sector, the active compounds can be incorporated, for example, into granules, oily spraying agents or slow release formulations.

The formulations are prepared in a known manner by mixing or diluting the active compounds according to the invention with solvents (for example xylene, chlorobenizenes, paraffins, methanol, ethanol, isopropanol or water), carriers (for example kaolins, aluminas, talc, chalk, highly disperse silicic acid and silicates), emulsifying agents (for example polyoxyethylene fatty acid esters, polyoxyethylene fatty alcohol ethers, alkylsulphonates and arylsulphonates) and dispersing agents (for example lignin, sulphite waste liquors and methylcellulose).

The active compounds according to the invention can be mixed with one another in the formulations or can also be used as mixtures with other known active compounds (for example sunscreen agents). The formulations in general contain between about 0.1 and about 95% (e.g., 0.1–95%) by weight of active compound, preferably between about 0.5 and about 90% (e.g., 0.5–90%).

For protection from arthropods such as blood-sucking insects or mites, the active compounds according to the invention are generally either applied to human or animal skin, or items of clothing and other objects are treated with the active compounds.

The active compounds according to the invention are also suitable as an additive to impregnating agents for, for example, textile webs, articles of clothing and packaging materials, and as an additive to polishing, cleaning and window-cleaning agents.

The compositions of the present invention contain a carrier material and the most effective stereoisomer repellent. The repellent of the present invention is generally applied with a carrier component. The carrier component can be a liquid or a solid material. As is known in the art, the vehicle or carrier to be used refers to a substrate such as a gel, polymers, or the like. All of these substrates have been used to release insect repellents and are well known in the art.

The most effective arthropod repellent stereoisomer, as used herein, means that stereoisomer(s) of a particular compound which is most effective in repelling arthropods in comparison to the other stereoisomers of that particular compound; in other words, that stereoisomer(s) which is most effective in reducing the number of arthropod bites. The amount of the most effective stereoisomer repellent used will be at least an effective amount. The term "effective amount," as used herein, means the minimum amount of the most effective stereoisomer repellent needed to reduce the number of arthropod (e.g., *Aedes aegypti* (Linnaeus)) bites on a treated area or object (e.g., mammalian skin which has been treated topically with the compound of the present invention) when compared to the same area or object which is untreated. Effective concentrations of the most effective stereoisomer repellent in the compositions may vary between about 0.1 and about 95% (e.g., 0.1–95%) by weight of active stereoisomer, preferably between about 0.5 and about 90% (e.g., 0.5–90%). Of course, the precise amount needed will vary in accordance with the particular repellent composition used; the type of area or object to be treated; the number of hours or days of repelling needed; and the environment in which the area or object is located. The precise amount of repellent can easily be determined by one skilled in the art given the teaching of this application. For example, one skilled in the art could follow the procedure utilized below.

For optimum results, the most effective stereoisomer repellent (e.g., (1S,2'S) stereoisomer of 1-(3-cyclohexen-1-ylcarbonyl)-2-methylpiperidine) should be used in a substantially pure form, that is, the stereoisomer must be free of undesirable contaminants that tend to mask or otherwise inhibit its effectiveness as a repellent. Generally, the most effective stereoisomer repellent is substantially free of other stereoisomers (e.g., those usually found in the racemate), e.g., in an enantiomeric excess of at least about 70% (e.g., 70%) excess or higher or at least about 80% (e.g., 80%) excess or higher, preferably at least about 90% (e.g., 90%) excess or higher, more preferably at least about 95% (e.g., 95%) excess or higher, more preferably at least about 97% (e.g., 97%) excess or higher, most preferably at least about 99% (e.g., 99%) excess or higher. The stereoisomer may be substantially enantiopure. Generally, the most effective stereoisomer repellent has high diastereochemical purity (about >5:1 (e.g., >5:1)), thus indicating that other diastereomers are present at about a 5 fold lower concentration than the most effective stereoisomer repellent; preferably the diastereochemical purity is about >10:1 (e.g., >10:1), more preferably the diastereochemical purity is about >15:1 (e.g., >15:1), most preferably the diastereochemical purity is about >40:1 (e.g., >40: 1).

The stereoisomer may be used with other repellents or arthropod control agents (e.g., insecticides, chemosterilants or the like). When used, these agents should be used in an amount which, as readily determined by one skilled in the arts, will not interfere with the effectiveness of the most effective stereoisomer repellent.

The following examples are intended only to further illustrate the invention and are not intended to limit the scope of the invention as defined by the claims.

EXAMPLES

A mosquito bioassay was used to address the configurational aspects of 220 stereoisomer repellence and nuclear magnetic resonance (NMR) spectroscopy and molecular mechanics calculations were applied to provide insight into the conformational aspects of 220 repellence.

Pure 220 stereoisomers were prepared and characterized earlier (Klun, J. A., et al., J. Med. Entomol., 37(1): 182–187 (2000) is incorporated by reference in its entirety). The stereoisomers have been evaluated toxicologically and approved for use in entomological studies with humans (Snodgrass, H. L., et al., Toxicology study No. 86-8104-98, The acute toxicity of the diastereomers of the insect repellent AI3-37220 (the 220 compound), June 1998, U.S. Army Center for Health Promotion and Preventative Medicine, Aberdeen Proving Ground, Md. 21010-5001). We applied the stereoisomers to the skin of humans to determine their individual repellent properties against a mosquito, *Aedes aegypti* (Linnaeus). In nature, *Ae. aegypti* is a vector of yellow fever and dengue virus. The mosquitoes were reared (Hoch, A. L., et al., J. A. Mosq. Control Assoc., 11: 172–175 (1995)) disease free at the Walter Reed Army Institute of Research. Mosquitoes were maintained in a 12 h:12 h photophase:scotophase at 27° C. and 80% RH. Mated females (5–15 days old) had access only to water 24 h and neither food nor water for another 24 h before testing. Laboratory bioassays were conducted by using 6-celled K & D modules and methods for quantitative evaluation of arthropod repellents on humans (Klun, J. A, et al., J. Med. Entomol., 37(1): 177–181 (2000) is incorporated by reference in its entirety). Repellent bioassays were done in a walk-in incubator (27° C. and 80% RH) in ambient fluorescent light from 0730 h to 1030 h over 3 days. Bioassays were replicated 36 times (2 volunteers with 12 replicates each and two volunteers with 6 replicates each) using a complete-randomized-block design for each replicate. Six treatments within a replicate consisted of each of the 220 stereoisomers alone, the 220 racemate and a control. The bioassay involved evaluation of the blood feeding (biting) frequency of mosquitoes in the six treatments. Each treatment (1.81 µg compound/µL ethanol) was pipetted onto a 4×5 cm rectangular area of the subjects' skin using 55 μL ethanol/treatment. Skin treated with ethanol was control. Thus, the dose of each treatment was 4.95 μg/cm² skin. The number of females biting (proboscis inserted into skin and/or observed blood-engorged specimens) within each of the 6 cells containing 5 mosquitoes/cell in a 2 min exposure period was recorded. Mosquitoes were used once in a test and then destroyed. Individual mosquitoes were scored as either having bit or not having bit during a trial. It was assumed that mosquitoes acted independently. That is, biting by one mosquito did not affect the probability of biting by other mosquitoes in the experiment. Sums of the numbers of biting and nonbiting mosquitoes in a group were treated as binomial data, and analyzed using standard log-linear methods. Log-linear models for the data sets were constructed using a stepwise procedure in S-Plus 4 (S-Plus 4 Guide to Statistics, 1997, Data analysis products division, MathSoft, Seattle, 877 pp.). The explanatory variables were treatment, subject, and frequency of biting and non biting mosquitoes. To determine which treatments differed, we used the method proposed by Levy (Levy, K. J., Psychological Bulletin 82: 174–176 (1975) to make pair-wise comparisons of the proportions of biting mosquitoes. This method controls for experiment-wise error rate, which we set to alpha=0.05.

Tests were also conducted using three additional blood feeding flies, Aedes albopictus, Anopheles stephensi, and Phlebotomus papatasi. Bioassays with these species were conducted using the same materials and methods used against Aedes aegypti except a lower dose of 2.5 μg compound/cm²skin was used in two cases; see Table 2.

NMR spectra were recorded using a Bruker QE Plus 300 MHz NMR spectrometer. Proton spectra were acquired with a spectral width of 3100 Hz and 4K data points. Chemical shifts are reported relative to tetramethylsilane. The spectra were collected at 25±5° C. No line broadening was used with the free induction decay signal. Solutions (0.5 mg/ml) were prepared of the individual (1R,2'S)- and (1S,2'S)-220 stereoisomers in deuterated solvents (benzene-$d_6$, acetone-$d_6$, $CDCl_3$ and $CD_2Cl_2$). The isomeric purity of the individual isomers has been previously reported by Klun et al. (J. Med. Entomol., 37(1): 182–187 (2000)). Molecular mechanics were done using MM3 (Allinger, N. L., et al., J. Am. Chem. Soc., 111: 8551–8566 (1989)) in the computational chemistry program, Alchemy (Tripos Inc., St. Louis, Mo.).

Results and Discussion:

Bioassay results obtained with Ae. aegypti are shown in Table 1. For these data sets, there were no differences among subjects, but significant differences among treatments. We report the total number of bites sustained within each treatment and the proportion of mosquitoes that bit in each treatment. The data are valuable because they provide insight into the chiral nature of the 220 chemoreceptor in this arthropod. The data show that the repellent chemoreceptor system in Ae. aegypti accommodates the (2'S) moiety more effectively than (2'R). Notably, stereoisomers (1S,2'S) and (1R,2'S) proved 2.8–3.1 and 1.6–1.8 times more repellent than the other stereoisomers, respectively. The racemate and (1S,2'R) and (1R,2'R) stereoisomers had repellent activities that were not significantly different from one another. If one considers the proportion biting values shown in Table 1 to represent the intrinsic repellent effect of each stereoisomer, the mean proportion biting value for all stereoisomers is 0.39, and this approximates the observed proportion biting value (0.45) for the racemate. This indicates that the affects of the individual stereoisomers isomers in the racemate are additive. The (1S,2'S) stereoisomer was 2.5 times more effective in suppressing Ae. Aegypti bites than the racemate at an equal dose and it is known that 220 racemate is more effective than deet. It follows that formulations of the (1S,2'S) asymmetric 220 repellent will likely exceed the effectiveness of deet against Ae. Aegypti and other blood-sucking arthropods. Large scale preparations of asymmetric repellents should be entirely feasible using existing asymmetric-synthesis technology such as that developed by Vries et al. (Vries, T., et al., Angewandte Chemie International Edition, 37: 2349–2354 (1998)).

Bioassay results obtained with Aedes albopictus and Anopheles stephensi mosquitoes and Phlebotomus papatasi sandfly against 220 stereoisomers are presented in Table 2. The responses of Aedes albopictus to the 220 stereiosomers were like those observed in tests with Aedes aegypti. The (1S,2'S) was 4 times more effective in suppressing Aedes albopictus bites than was the racemate, and although the (1R,2'S) was less effective a repellent than (1S,2'S), it was more effective than the (1S,2'R) and (1R,2'R) stereoisomers. Like Aedes aegypti, the Aedes albopictus repellent chemoreceptor system accommodates the (2'S) moiety more effectively than (2'R). In bioassays with the mosquito, Anopheles stephensi, and the sandfly, Phlebotomus papatasi, (1S,2'S) was always effective most effective in repelling bites, and although differences were not statistically significant the order the ascending order of stereoisomer effectiveness was same as seen in Aedes aegypti and Aedes albopictus. Taken as a whole, the bioassay results convincingly show that it is possible to select the most effective arthropod repellent from stereoisomers of a compound. The extent of repellent advantage gained by selecting the most effective stereoisomer may vary depending on the species involved.

Chemical structures containing six-membered aliphatic carbon rings can exist in multiple conformations (Streitwieser, Jr., A., et al., 1981, Introduction to organic chemistry (2nd Edition), Macmillan Publishing Co., New York, N.Y., p87). Because all four isomers of 220 contain the identical constituents, one might incorrectly assume that the conformation of the rings in all four compounds would be similar. NMR has been used to investigate preferred conformations in solution; broad peaks are evidence of multiple conformations simultaneously present and stable within the time frame of the experiment (Harris, R. K., 1986, Nuclear Magnetic Resonance Spectroscopy, A Physicochemical View., Longman Scientific & Technical, Essex, England, p. 119–131). The room temperature NMR spectra of (1S,2'S)-220 isomer (FIG. 2A) and of (1R,2'S)-220 isomer (FIG. 2B) present clear evidence that the 2'-ring (0.9–2.2 ppm) in each isomer exists in multiple conformations in solution. Broadening of the 2'-ring protons occurred in all of the solvents investigated, demonstrating the broadening is solvent independent.

Figure 2:
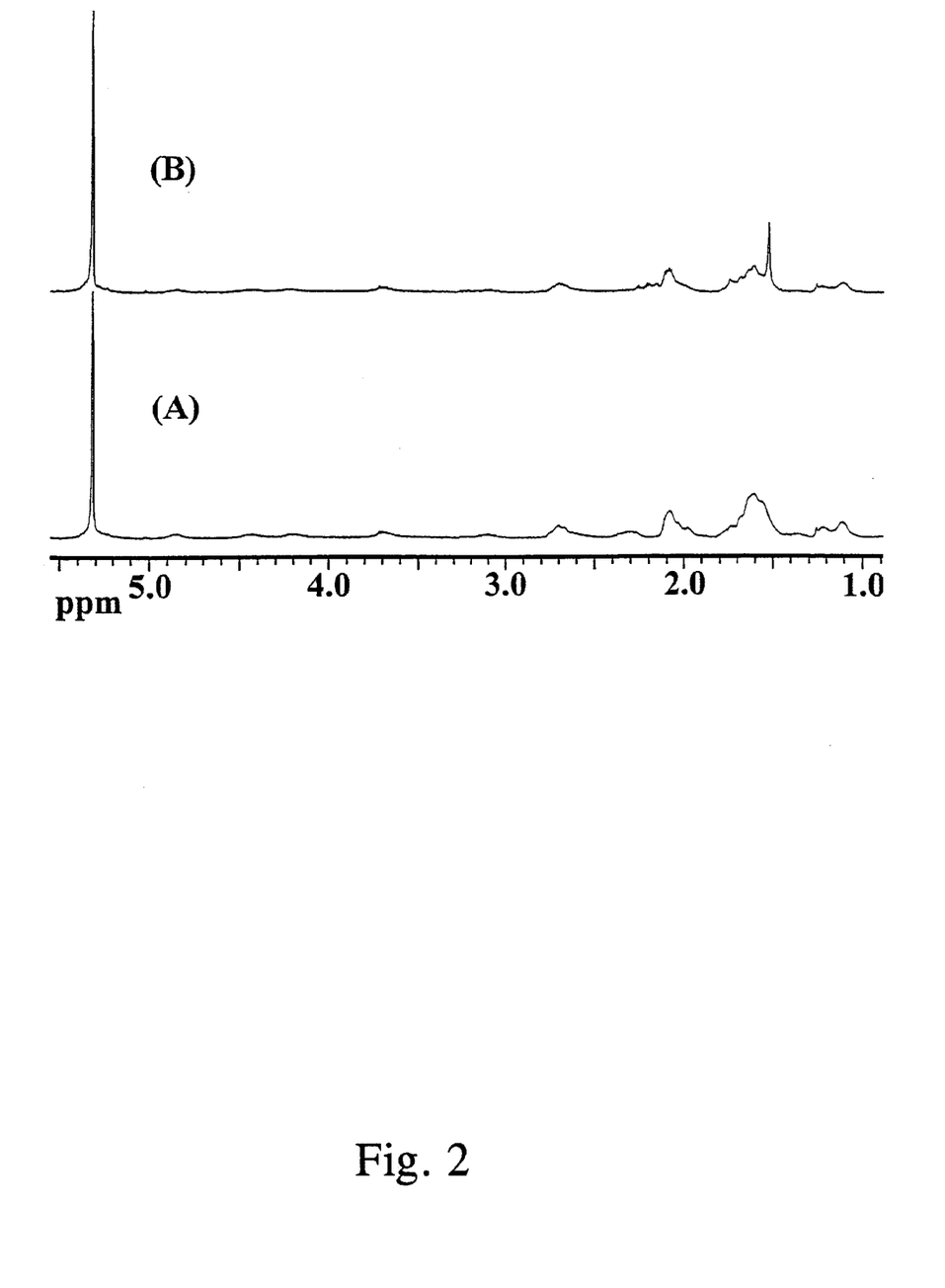
FIG. 2 shows NMR spectra of (1S,2'S) (A) and (1R,2'S) (B) stereoisomers of 220.

The (2'S)-ring is a structural feature in common between the most repellent isomer ((1S,2'S)-220) and the second most repellent isomer ((1R,2'S)-220). Yet, under identical conditions, the NMR data shows the conformation of that ring is significantly different from one isomer to the other. The methyl peak on the 2'S-ring at 1.5 ppm in (1S,2'S)-220 isomer is not readily distinguishable from the other overlapping aliphatic proton peaks from 1.2–1.6 ppm. In contrast, the corresponding methyl peak at 1.5 ppm is markedly sharp in (1R,2'S)-220 isomer. The sharp methyl peak is evidence that multiple aliphatic ring conformations exchange significantly more slowly in the (1R,2'S)-220 isomer configuration than in the (1S,2'S)-220 isomer configuration. The conformation of the methyl group clearly can be an important component of the molecular fit at the repellent-receptor site.

The broadness of the NMR aliphatic ring proton peaks and the methyl peak of the (2'S)-ring can be readily explained from the molecular mechanics results. Because the energy minimized structures of each of the two stable conformations are essentially the same, both forms co-exist in equal abundance simultaneously. In (1S,2'S)- the average conformation is a distribution of multiple intermediate forms interchanging between these two conformations of the (2'S)-aliphatic ring. The 2'-ring methyl NMR peak is also broad in the (1S,2'S)-220 isomer and this is evidence for an abundance of intermediate conformations.

Figure 3:
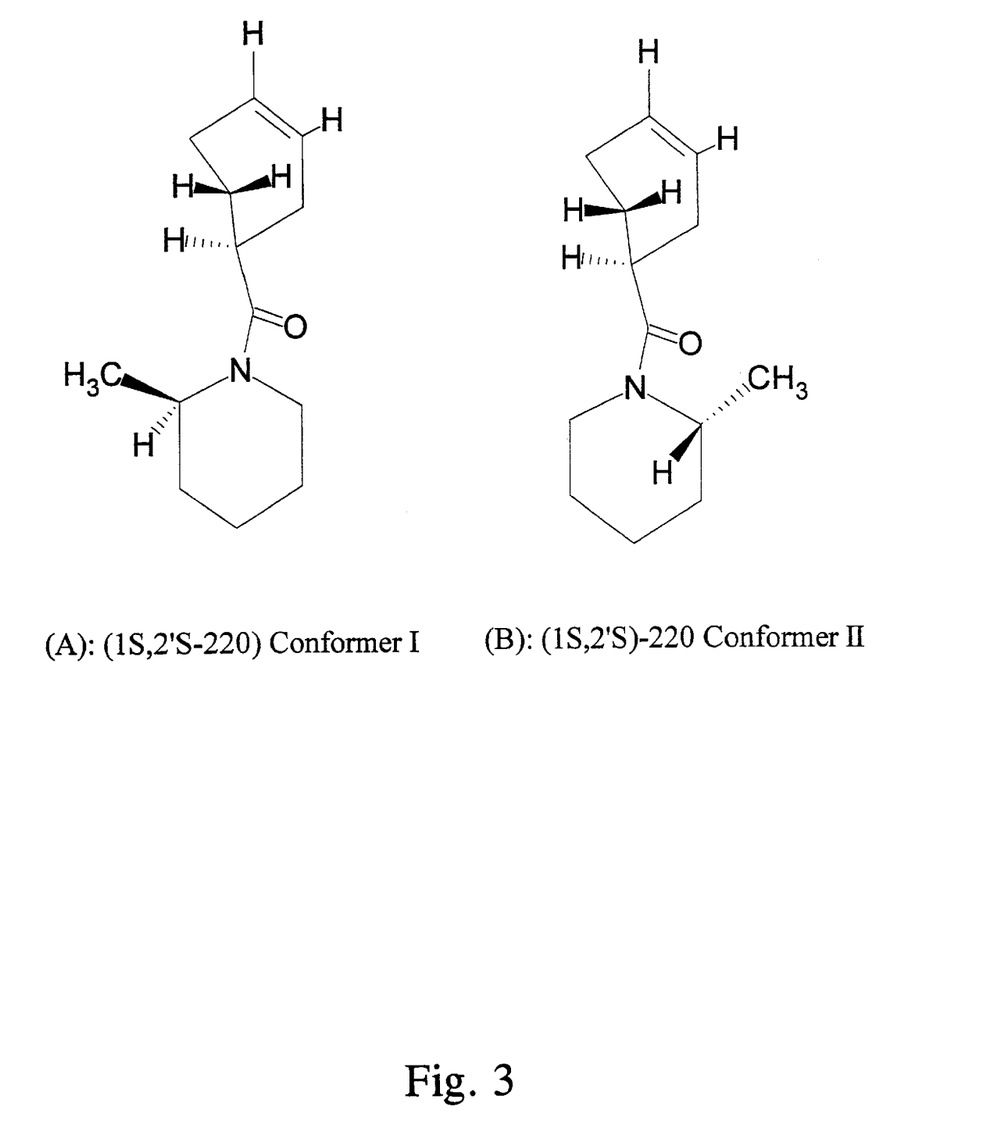
FIG. 3 shows molecular mechanics model showing the two stable conformations of the (1S,2'S)-stereoisomer configuration.

Molecular mechanics calculations demonstrated that two stable conformations of the (2'S)-ring exist independent of the (1S) or (1R) configuration. The structure of these conformations for the (1S,2'S)-isomer is shown in FIGS. 3A and 3B. Restricted rotation due to steric hindrance at the amide moiety deters interconversion of the two conformations. Calculations showed that (1R,2'R)-220 isomer has restricted rotation equivalent to the (1S,2'S)-220 isomer, and that it also occurs in two stable conformations that are mirror images of the (1S,2'S)-220 isomer. However, as shown in Table 1, (1R,2'R)-220 isomer was significantly less effective as a repellent against *Ae. Aegypti*; thus, the (2'S)-ring is required for proper interact with the repellent receptor, and correct conformation and configuration at the 2'-chiral center are essential stereochemical components for (1S,2'S)-220 repellent activity.

All of the references cited herein are incorporated by reference in their entirety. The following U.S. Patents are also incorporated by reference in their entirety: U.S. Pat. No. 5,008,261; 4,797,408; and 4,621,143.

Thus, in view of the above, the present invention concerns (in part) the following:

A method for selecting the most effective arthropod repellent from stereoisomers of a compound, comprising or consisting essentially of or consisting of testing each stereoisomer of said compound for its effectiveness as an arthropod repellent against an arthropod of a particular genus and species, comparing the test results and selecting the most effective arthropod repellent stereoisomer from said stereoisomers of said compound, wherein said compound is a piperidine analog of the formula (I)

in which $R_2$, $R_3$, $R_4$, $R_5$ and $R_6$ may be the same or different and represent hydrogen, methyl, ethyl, isopropyl, or butyl groups, wherein said methyl, ethyl, isopropyl, or butyl groups are optionally substituted in their primary or secondary position with a hydroxyl (—OH) group, and $R_1$ represents unbranched or branched C1–8 alkanes, unbranched or branched C1–8 alkenes, C5–8 cycloalkanes, C5–8 cycloalkanes, methyl substituted C5–8 cycloalkanes, or methyl substituted C5–8 cycloalkenes or $R_1$ is —O—$R_7$ wherein a carbon atom of $R_7$ is attached to the O of —O—$R_7$ and wherein $R_7$ represents unbranched C1–8 alkanes, branched C1–8 allanes, unbranched C1–8 alkenes, branched C1–8 alkenes, C5–8 cycloalkanes, C5–8 cycloalkenes, methyl substituted C5–8 cycloalkanes, or methyl substituted C5–8 cycloalkenes, and wherein said compound has at least one asymmetric center.

The above method, wherein said compound has one or more (e.g., one or two) asymmetric centers.

The above method, wherein $R_2$, $R_3$, $R_4$, $R_5$, and $R_6$ may be the same or different and are hydrogen, methyl or —CH$_2$—CH$_2$—OH and $R_1$ is 3-cyclohexene, —CH=C(CH$_3$)$_2$ or —O—$R_7$ where $R_7$ is a unbranched or branched $C_4$alkane.

The above method, wherein $R_1$ is —O—$R_7$ where $R_7$ is a $C_4$ unbranched alkane and O- is attached to carbon atom number 2 of said $C_4$ alkane.

The above method, wherein said compound is selected from the group consisting of 1-(3-cyclohexen-1-ylcarbonyl)piperidine, 1-(2-butoxycarbonyl)-2-(2-hydroxyethyl)-piperidine, and 1-(3-cyclohexen-1-ylcarbonyl)-2-methylpiperidine.

The above method, wherein said compound is 1-(3-cyclohexen-1-ylcarbonyl)-2-methylpiperidine.

The above method, wherein said arthropod of a particular genus and species is Aedes species.

The above method, wherein said arthropod of a particular genus and species is selected from the group consisting of *Aedes aegypti, Aedes albopictus, Anopheles stephensi*, and *Phlebotomus papatasi*.

The above method, wherein said arthropod of a particular genus and species is *Aedes aegypti* or *Aedes albopictus*, wherein said compound is 1-(3-cyclohexen-1-ylcarbonyl)-2-methylpiperidine, and wherein said most effective arthropod repellent stereoisomer is the (1S,2'S) stereoisomer of 1-(3-cyclohexen-1-ylcarbonyl)-2-methylpiperidine.

The above method, wherein each stereoisomer of said compound is present in an enantomeric excess of at least about 70% or higher.

The above method, wherein each stereoisomer of said compound is present in an enantomeric excess of at least about 80% or higher.

The above method, wherein each stereoisomer of said compound is present in an enantomeric excess of at least about 90% or higher.

The above method, wherein each stereoisomer of said compound is present in an enantomeric excess of at least about 95% or higher.

The above method, wherein each stereoisomer of said compound is present in an enantomeric excess of at least about 97% or higher.

The above method, wherein each stereoisomer of said compound is present in an enantomeric excess of at least about 99% or higher.

The above method, wherein each stereoisomer of said compound is substantially enantiopure.

The above method, wherein each stereoisomer of said compound has a diastereochemical purity of about >5:1.

The above method, wherein each stereoisomer of said compound has a diastereochemical purity of about >10:1.

The above method, wherein each stereoisomer of said compound has a diastereochemical purity of about >40:1.

The above method, further comprising isolating each stereoisomer of said compound or preparing each stereoisomer of said compound.

The above method, wherein said arthropod of a particular genus and species is *Aedes aegypti* or *Aedes albopictus*, wherein said compound is 1-(3-cyclohexen-1-ylcarbonyl)-2-methylpiperidine, and wherein said most effective arthropod repellent stereoisomer is the (1S,2'S) stereoisomer of 1-(3-cyclohexen-1-ylcarbonyl)-2-methylpiperidine.

A composition for repelling arthropods, comprising or consisting essentially of or consisting of a carrier material and an arthropod repelling effective amount of a stereoisomer of a compound, wherein said stereoisomer is selected by the above method.

The above composition, wherein said stereoisomer is present in an enantomeric excess of at least about 70% or higher The above composition, wherein said stereoisomer is present in an enantomeric excess of at least about 80% or higher.

The above composition, wherein said stereoisomer is present in an enantomeric excess of at least about 90% or higher.

The above composition, wherein said stereoisomer is present in an enantomeric excess of at least about 95% or higher.

The above composition, wherein said stereoisomer is present in an enantomeric excess of at least about 97% or higher.

The above composition, wherein said stereoisomer is present in an enantomeric excess of at least about 99% or higher.

The above composition, wherein said stereoisomer is substantially enantiopure.

The above composition, wherein each stereoisomer of said compound has a diastereochemical purity of about >5:1.

The above composition, wherein each stereoisomer of said compound has a diastereochemical purity of about >10:1.

The above composition, wherein each stereoisomer of said compound has a diastereochemical purity of about >40:1.

A method for repelling arthropods from a mammal, comprising or consisting essentially of or consisting of treating a mammal with an arthropod repelling composition consisting essentially of a carrier material and an arthropod repelling effective amount of a stereoisomer of a compound, wherein said stereoisomer is selected by a method for selecting the most effective arthropod repellent from stereoisomers of a compound comprising or consisting essentially of or consisting of testing each stereoisomer of said compound for its effectiveness as an arthropod repellent against an arthropod of a particular genus and species, comparing the test results and selecting the most effective arthropod repellent stereoisomer from said stereoisomers of said compound, wherein said compound is a piperidine analog of the formula (I)

in which $R_2$, $R_3$, $R_4$, $R_5$ and $R_6$ may be the same or different and represent hydrogen, methyl, ethyl, isopropyl, or butyl groups, wherein said methyl, ethyl, isopropyl, or butyl groups are optionally substituted in their primary or secondary position with a hydroxyl (—OH) group, and $R_1$ represents unbranched or branched C1–8 alkanes, unbranched or branched C1–8 alkenes, C5–8 cycloalkanes, C5–8 cycloalkenes, methyl substituted C5–8 cycloalkanes, or methyl substituted C5–8 cycloalkenes or $R_1$ is —O—$R_7$ wherein a carbon atom of $R_7$ is attached to the O of —O—$R_7$ and wherein $R_7$ represents unbranched C1–8 alkanes, branched C1–8 alkanes, unbranched C1–8 alkenes, branched C1–8 alkenes, C5–8 cycloalkanes, C5–8 cycloalkenes, methyl substituted C5–8 cycloalkanes, or methyl substituted C5–8 cycloalkenes, and wherein said compound has at least one asymmetric center.

The above method, wherein said compound has one or more (e.g., one or two) asymmetric centers.

The above method, wherein $R_2$, $R_3$, $R_4$, $R_5$, and $R_6$ may be the same or different and are hydrogen, methyl or —CH$_2$—CH$_2$—OH and $R_1$ is 3-cyclohexene, —CH=C(CH$_3$)$_2$ or —O—$R_7$ where $R_7$ is a unbranched or branched $C_4$ alkane.

The above method, wherein $R_1$ is —O—$R_7$ where $R_7$ is a $C_4$ unbranched alkane and O— is attached to carbon atom number 2 of said $C_4$ alkane.

The above method, wherein said compound is selected from the group consisting of 1-(3-cyclohexen-1-ylcarbonyl) piperidine, 1-(2-butoxycarbonyl)-2-(2-hydroxyethyl)-piperidine, and 1-(3-cyclohexen-1-ylcarbonyl)-2-methylpiperidine.

The above method, wherein said compound is 1-(3-cyclohexen-1-ylcarbonyl)-2-methylpiperidine.

The above method, wherein most effective arthropod repellent stereoisomer is the (1S,2'S) stereoisomer of 1-(3-cyclohexen-1-ylcarbonyl)-2-methylpiperidine.

The above method, wherein each stereoisomer of said compound is present in an enantomeric excess of at least about 70% or higher.

The above method, wherein each stereoisomer of said compound is present in an enantomeric excess of at least about 80% or higher.

The above method, wherein each stereoisomer of said compound is present in an enantomeric excess of at least about 90% or higher.

The above method, wherein each stereoisomer of said compound is present in an enantomeric excess of at least about 95% or higher.

The above method, wherein each stereoisomer of said compound is present in an enantomeric excess of at least about 97% or higher.

The above method, wherein each stereoisomer of said compound is present in an enantomeric excess of at least about 99% or higher.

The above method, wherein each stereoisomer of said compound is substantially enantiopure.

The above method, further comprising isolating each stereoisomer of said compound or preparing each stereoisomer of said compound.

The above method, wherein each stereoisomer of said compound has a diastereochemical purity of about >5:1.

The above method, wherein each stereoisomer of said compound has a diastereochemical purity of about >10:1.

The above method, wherein each stereoisomer of said compound has a diastereochemical purity of about >40:1.

The above method, wherein said arthropod of a particular genus and species is Aedes species.

The above method, wherein said arthropod of a particular genus and species is selected from the group consisting of *Aedes aegypti, Aedes albopictus, Anopheles stephensi*, and *Phlebotomus papatasi*.

The above method, wherein said arthropods are *Aedes aegypti* or *Aedes albopictus*, wherein said compound is 1-(3-cyclohexen-1-ylcarbonyl)-2-methylpiperidine, and wherein said most effective arthropod repellent stereoisomer is the (1S,2'S) stereoisomer of 1-(3-cyclohexen-1-ylcarbonyl)-2-methylpiperidine.

A method for repelling arthropods from a mammal, comprising treating a mammal with an arthropod repelling composition consisting essentially of a carrier material and an arthropod repelling effective amount of the (1S,2'S) stereoisomer of 1-(3-cyclohexen-1-ylcarbonyl)-2-methylpiperidine, wherein said arthropods are Aedes species.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A method for selecting the most effective arthropod repellent from stereoisomers of a compound, comprising:
   testing each stereoisomer of said compound for its effectiveness as an arthropod repellent against an arthropod,
   comparing the test results and selecting the most effective arthropod repellent stereoisomer from said stereoisomers of said compound,
   wherein said compound is a piperidine analog of the formula (I)

in which $R_2$, $R_3$, $R_4$, $R_5$ and $R_6$ may be the same or different and represent hydrogen, methyl, ethyl, isopropyl, or butyl groups, wherein said methyl, ethyl, isopropyl, or butyl groups are optionally substituted in their primary or secondary position with a hydroxyl (—OH) group, and $R_1$ represents unbranched or branched C1–8 alkanes, unbranched or branched C1–8 alkenes, C5–8 cycloalkanes, C5–8 cycloalkenes, methyl substituted C5–8 cycloalkanes, or methyl substituted C5–8 cycloalkenes or $R_1$ is —O—$R_7$ wherein a carbon atom of $R_7$ is attached to the O of —O—$R_7$ and wherein $R_7$ represents unbranched C1–8 alkanes, branched C1–8 alkanes, unbranched C1–8 alkenes, branched C1–8 alkenes, C5–8 cycloalkanes, C5–8 cycloalkenes, methyl substituted C5–8 cycloalkanes, or methyl substituted C5–8 cycloalkenes, and wherein said compound has at least one asymmetric center.

2. The method according to claim 1, wherein said compound has one or more asymmetric centers.

3. The method according to claim 1, wherein $R_2$, $R_3$, $R_4$, $R_5$, and $R_6$ may be the same or different and are hydrogen, methyl or —CH$_2$—CH$_2$—OH and $R_1$ is 3-cyclohexene, —CH=C(CH$_3$)$_2$ or —O—$R_7$ where $R_7$ is a unbranched or branched $C_4$ alkane.

4. The method according to claim 3, wherein $R_1$ is —O—$R_7$ where $R_7$ is a $C_4$ unbranched alkane and O— is attached to carbon atom number 2 of said $C_4$ alkane.

5. The method according to claim 1, wherein said compound is selected from the group consisting of 1-(3-cyclohexen-1-ylcarbonyl)piperidine, 1-(2-butoxycarbonyl)-2-(2-hydroxyethyl)-piperidine, and 1-(3-cyclohexen-1-ylcarbonyl)-2-methylpiperidine.

6. The method according to claim 5, wherein said compound is 1-(3-cyclohexen-1-ylcarbonyl)-2-methylpiperidine.

7. The method according to claim 6, wherein said most effective arthropod repellent stereoisomer is the (1S,2'S) stereoisomer of 1-(3-cyclohexen-1-ylcarbonyl)-2-methylpiperidine.

8. The method according to claim 1, wherein each stereoisomer of said compound is present in an enantiomeric excess of at least about 70% or higher, or at least about 80% or higher, or at least about 90% or higher, or at least about 95% or higher, or at least about 97% or higher, or at least about 99% or higher.

9. The method according to claim 1, wherein each stereoisomer of said compound is substantially enantiopure.

10. The method according to claim 1, wherein said arthropod is selected from the group consisting of *Aedes aegypti, Aedes albopictus, Anopheles stephensi*, and *Phlebotomus papatasi*.

11. The method according to claim 1, wherein said arthropod is *Aedes aegypti* or *Aedes albopictus*, wherein said compound is 1-(3-cyclohexen-1-ylcarbonyl)-2-methylpiperidine, and wherein said most effective arthropod repellent stereoisomer is the (1S,2'S) stereoisomer of said 1-(3-cyclohexen-1-ylcarbonyl)-2-methylpiperidine.

12. A method for repelling arthropods from a mammal, comprising treating said mammal with an arthropod repelling composition consisting essentially of a carrier material and an arthropod repelling effective amount of a stereoisomer of a compound, wherein said stereoisomer is selected by the method according to claim 1.

13. The method according to claim 12, wherein each stereoisomer of said compound is present in an enantiomeric excess of at least about 70% or higher.

14. The method according to claim 12, wherein each stereoisomer of said compound is present in an enantiomeric excess of at least about 80% or higher.

15. The method according to claim 12, wherein each stereoisomer of said compound is present in an enantiomeric excess of at least about 90% or higher.

16. The method according to claim 12, wherein each stereoisomer of said compound is present in an enantiomeric excess of at least about 95% or higher.

17. The method according to claim 12, wherein each stereoisomer of said compound is present in an enantiomeric excess of at least about 97% or higher.

18. The method according to claim 12, wherein each stereoisomer of said compound is present in an enantiomeric excess of at least about 99% or higher.

19. The method according to claim 12, wherein each stereoisomer of said compound is substantially enantiopure.

20. The method according to claim 12, wherein said arthropod is selected from the group consisting of *Aedes aegypti, Aedes albopictus, Anopheles stephensi*, and *Phlebotomus papatasi*.

21. The method according to claim 12, wherein said arthropod is *Aedes aegypti* or *Aedes albopictus*, wherein said compound is 1-(3-cyclohexen-1-ylcarbonyl)-2-methylpiperidine, and wherein said most effective arthropod repellent stereoisomer is the (1S,2'S) stereoisomer of said 1-(3-cyclohexen-1-ylcarbonyl)-2-methylpiperidine.

* * * * *